US006558612B1

(12) United States Patent
Hubbard

(10) Patent No.: US 6,558,612 B1
(45) Date of Patent: May 6, 2003

(54) PROCESS FOR PRODUCING SPHERICAL BIOCOMPATIBLE CERAMIC PARTICLES

(75) Inventor: William G. Hubbard, East Troy, MI (US)

(73) Assignee: Bioform Inc., Franksvile, WI (US)

( * ) Notice: Subject to any disclaimer, the term of this patent is extended or adjusted under 35 U.S.C. 154(b) by 0 days.

(21) Appl. No.: 09/187,924

(22) Filed: Nov. 6, 1998

Related U.S. Application Data

(63) Continuation of application No. 08/538,444, filed on Oct. 3, 1995, now Pat. No. 5,922,025, which is a division of application No. 08/159,071, filed on Nov. 29, 1993, which is a continuation of application No. 07/999,411, filed on Jan. 21, 1993, now abandoned, which is a continuation-in-part of application No. 07/833,874, filed on Feb. 11, 1992, now abandoned.

(51) Int. Cl.[7] .............................................. C04B 33/32

(52) U.S. Cl. ..................................... 264/654; 264/669

(58) Field of Search ........................... 264/13, 15, 628, 264/654, 666, 669, 670, 681

(56) References Cited

U.S. PATENT DOCUMENTS

| 3,703,575 A | 11/1972 | Thiele ............................. 3/1 |
| 4,107,288 A | 8/1978 | Oppenheim et al. .......... 424/22 |
| 4,123,091 A | 10/1978 | Cosentino .................... 285/39 |

(List continued on next page.)

FOREIGN PATENT DOCUMENTS

| CA | 2029338 | 5/1991 |
| CH | 643732 | 1/1978 |
| EP | 0196143 | 10/1986 |
| EP | 416761 | 3/1991 |
| EP | 543765 | 5/1993 |
| JP | 61101447 | 5/1986 |
| JP | 6211459 | 1/1987 |
| NL | 8304129 | 7/1985 |

OTHER PUBLICATIONS

Reed, Principles of Ceramics Processing, Second Edition, John Wiley & Sons, Table of Contents, 1995.*
Misek, et al., "The Inflammatory Response to Different Shaped Hydroxylapatite Particles Implanted In Soft Tissue," 9th Annual Meeting of the Society of Biomaterials, Apr. 27–May 1, 1983.
Cacitite 4060 Dense Nonresorbable Bone Graft Material for Filling Periodontal and Pontic Area Defects, Calcitek, Inc., Calsbad, California (Apr. 1988).
Orthomatrix Non–resorbable Hydroxylapatite Bone Graft Substitute, Lifecore Biomedical, Inc., Chaska, Minnesota (Dec. 1992).
Frialit Hydroxylapatit–Keramik, Friedricksfeld Medizin—Technik (date unknown).

(List continued on next page.)

*Primary Examiner*—Christopher A. Fiorilla
(74) *Attorney, Agent, or Firm*—Michael D. Rechtin; Foley & Lardner

(57) ABSTRACT

A permanent, biocompatible material for soft tissue augmentation. The biocompatible material comprises a matrix of smooth, round, finely divided, substantially spherical particles of a biocompatible ceramic material, close to or in contact with each other, which provide a scaffold or lattice for autogenous, three dimensional, randomly oriented, non-scar soft tissue growth at the augmentation site. The augmentation material can be homogeneously suspended in a biocompatible, resorbable lubricious gel carrier comprising a polysaccharide. This serves to improve the delivery of the augmentation material by injection to the tissue site where augmentation is desired. The augmentation material is especially suitable for urethral sphincter augmentation, for treatment of incontinence, for filling soft tissue voids, for creating soft tissue blebs, for the treatment of unilateral vocal cord paralysis, and for mammary implants. It can be injected intradermally, subcutaneously or can be implanted.

14 Claims, 2 Drawing Sheets

U.S. PATENT DOCUMENTS

| | | | |
|---|---|---|---|
| 4,197,104 A | * 4/1980 | Krystyniak et al. | 65/21 |
| 4,440,754 A | 4/1984 | Sorenson | 424/140 |
| 4,497,075 A | 2/1985 | Niwa et al. | 3/19 |
| 4,518,430 A | 5/1985 | Brown et al. | 106/35 |
| 4,551,436 A | * 11/1985 | Johnson et al. | 501/90 |
| 4,693,986 A | 9/1987 | Vit et al. | 501/1 |
| 4,803,075 A | 2/1989 | Wallace et al. | 404/423 |
| 4,836,994 A | * 6/1989 | Inoue et al. | 423/308 |
| 4,917,702 A | * 4/1990 | Scheicher et al. | 623/16 |
| 4,952,323 A | 8/1990 | Nakabayash et al. | 210/691 |
| 5,030,391 A | 7/1991 | Sumita et al. | 264/5 |
| 5,034,352 A | 7/1991 | Vit et al. | 501/1 |
| 5,035,711 A | 7/1991 | Aoki et al. | 623/11 |
| 5,053,212 A | 10/1991 | Constantz et al. | 423/305 |
| 5,067,965 A | 11/1991 | Ersek et al. | 623/66 |
| 5,075,360 A | 12/1991 | Fitt et al. | 524/48 |
| 5,108,956 A | * 4/1992 | Inoue et al. | 501/1 |
| 5,126,141 A | 6/1992 | Henry | 424/423 |
| 5,140,016 A | 8/1992 | Goldberg et al. | 514/57 |
| 5,141,561 A | 8/1992 | Ledard et al. | 106/35 |
| 5,143,724 A | 9/1992 | Leshchiner et al. | 424/78.04 |
| 5,149,368 A | 9/1992 | Liu et al. | 424/602 |
| 5,152,836 A | 10/1992 | Hirano et al. | 106/690 |
| 5,205,928 A | 4/1993 | Inove et al. | 210/198.2 |
| 5,217,699 A | 6/1993 | Tagaya et al. | 423/308 |
| 5,246,698 A | 9/1993 | Leshchiner et al. | 424/78.08 |
| 5,266,248 A | 11/1993 | Ohtsuka et al. | 264/44 |
| 5,399,351 A | 3/1995 | Leshchiner et al. | 424/422 |
| 5,441,635 A | 8/1995 | Ichitsuka | 210/198.2 |
| 5,451,406 A | 9/1995 | Lawin et al. | 424/423 |
| 5,480,644 A | 1/1996 | Freed | 424/436 |
| 5,490,984 A | 2/1996 | Freed | 424/436 |
| 5,523,291 A | 6/1996 | Janzen et al. | 514/21 |
| 5,571,182 A | 11/1996 | Ersek et al. | 623/11 |
| 5,573,771 A | 11/1996 | Geistlich et al. | 424/422 |
| 5,591,453 A | 1/1997 | Ducheyne et al. | 424/484 |
| 5,626,861 A | 5/1997 | Laurencin et al. | 424/426 |
| 5,637,101 A | 6/1997 | Shillington | 604/242 |
| 5,702,677 A | 12/1997 | Shimp et al. | 423/308 |
| 5,709,875 A | 1/1998 | Lebugle et al. | 424/426 |
| 5,752,974 A | 5/1998 | Rhee et al. | 606/214 |
| 5,766,618 A | 6/1998 | Laurencin et al. | 424/426 |
| 5,792,478 A | 8/1998 | Lawin et al. | 424/502 |
| 5,827,937 A | 10/1998 | Agerup | 536/123.12 |
| 5,837,752 A | 11/1998 | Shastri et al. | 523/116 |
| 5,853,398 A | 12/1998 | Lal et al. | 604/250 |
| 5,854,382 A | 12/1998 | Loomis | 528/354 |
| 5,861,176 A | 1/1999 | Ducheyne et al. | 424/486 |
| 6,165,514 A | 12/2000 | Bockman et al. | 424/495 |
| 6,306,297 B1 | * 10/2001 | Ichitsuka et al. | 210/198.2 |

OTHER PUBLICATIONS

Hy–Apatite, An Unique Calciumhydroxyapatite, Euro Crystals (date unknown).

Alveograf Non–resorbable Bone–Grafina Implant Material, Cook–Waite (date unknown).

OsteoGraft Hydroxylapatite, Ceramed (date unknown).

Hydradtion and Hardneing of Brushi and Monetite; Yogyo–Kyokai–Shi, vol. 95, No. 2, pp. 284–285 (1987) (No month available).

Biomaterials, vol. 10, pp. 634–638 (1989) (No month available).

* cited by examiner

PROCESS FOR PRODUCING SPHERICAL BIOCOMPATIBLE CERAMIC PARTICLES

This is a continuation of application Ser. No. 08/538,444 filed Oct. 3, 1995, U.S. Pat. No. 5,922,025 which is a divisional of application Ser. No. 08/159,071, filed Nov. 29, 1993, which is a continuation of application Ser. No. 07/999,411 filed Jan. 21, 1993, now abandoned, which is a continuation-in-part of application Ser. No. 07/833,874, filed Feb. 11, 1992, now abandoned, the disclosures of which are all incorporated herein by reference.

FIELD OF THE INVENTION

This invention relates to biocompatible compositions for soft tissue augmentation more specifically urethral sphincter augmentation for treatment of incontinence, for filling soft tissue voids or creating soft tissue blebs, for mammary implants, and for the treatment of unilateral vocal cord paralysis.

BACKGROUND OF THE INVENTION

Examples of biocompatible materials that have been proposed for use in augmenting soft tissue in the practice of plastic and reconstructive surgery, include collagen, gelatin beads, beads of natural or synthetic polymers such as polytetrafluoroethylene, silicone rubber and various hydrogel polymers, such as polyacrylonitrile-polyacrylamide hydrogels.

Most often, the biomaterials are delivered to the tissue site where augmentation is desired by means of an injectable composition which comprises the biomaterial and a biocompatible fluid that acts as a lubricant to improve the injectability of the biomaterial suspension. The injectable biomaterial compositions can be introduced into the tissue site by injection from a syringe intradermally or subcutaneously into humans or other mammals to augment soft tissue, to correct congenital anomalies, acquired defects or cosmetic defects. They may also be injected into internal tissues such as tissue defining sphincters to augment such tissue in the treatment of incontinence, and for the treatment of unilateral vocal cord paralysis.

U.K Patent Application No. 2,227,176 to Ersek et al, relates to a microimplantation method for filling depressed scars, unsymmetrical orbital floors and superficial bone defects in reconstructive surgery procedures using microparticles of about 20 to 3,000 microns which may be injected with an appropriate physiologic vehicle and hypodermic needle and syringe in a predetermined locus such as the base of depressed scars, beneath skin areas of depression and beneath perichondrium or periosteum in surface irregularities of bone and cartilage. Textured microparticles can be used, including silicone, polytetrafluoroethylene, ceramics or other inert substances. In those instances wherein the requirement is for hard substances, biocompatible material such as calcium salts including hydroxyapatite or crystalline materials, biocompatible ceramics, biocompatible metals such as stainless steel particles or glass may be utilized. Appropriate physiological vehicles have been suggested, including saline, various starches, polysaccharides, and organic oils or fluids.

U.S. Pat. No. 4,803,075 to Wallace et al, relates to an injectable implant composition for-soft tissue augmentation comprising an aqueous suspension of a particulate biocompatible natural or synthetic polymer and a lubricant to improve the injectability of the biomaterial suspension.

U.S. Pat. No. 4,837,285 to Berg et al, relates to a collagen-based composition for augmenting soft tissue repair, wherein the collagen is in the form of resorbable matrix beads having an average pore size of about 50 to 350 microns, with the collagen comprising up to about 10% by volume of the beads.

U.S. Pat. No. 4,280,954 to Yannas et al, relates to a collagen-based composition for surgical use formed by contacting collagen with a mucopolysaccharide under conditions at which they form a reaction product and subsequently covalently crosslinking the reaction product.

U.S. Pat. No. 4,352,883 to Lim discloses a method for encapsulating a core material, in the form of living tissue or individual cells, by forming a capsule of polysaccharide gums which can be gelled to form a shape retaining mass by being exposed to a change in conditions such as a pH change or by being exposed to multivalent cations such as calcium.

Namiki, "Application of Teflon Paste for Urinary Incontinence-Report of Two Cases", *Urol. Int.*, Vol. 39, pp. 280–282, (1984), discloses the use of a polytetrafluoroethylene paste injection in the subdermal area to treat urinary incontinence.

Drobeck et al, "Histologic Observation of Soft Tissue Responses to Implanted, Multifaceted Particles and Discs of Hydroxylapatit", *Journal of Oral Maxillofacial Surgery*, Vol. 42, pp. 143–149, (1984), discloses that the effects on soft tissue of long and short term implants of ceramic hydroxylapatite implanted subcutaneously in rats and subcutaneously and subperiosteally in dogs. The inventions consisted of implanting hydroxylapatite in various sizes and shapes for time periods ranging from seven days to six years to determine whether migration and/or inflammation occurred.

Misiek et al., "Soft Tissue Responses to Hydroxylapatite Particles of Different Shapes", *Journal of Oral Maxillofacial Surgery*, Vol. 42, pp. 150–160, (1984), discloses that the implantation of hydroxylapatite in the form of sharp edged particles or rounded particles in the buccal soft tissue pouches produced inflammatory response at the implant sites with both particle shapes. Each of the particles weighed 0.5 grams. However, inflammation resolved at a faster rate at the sites implanted with the rounded hydroxylapatite particles.

Shimizu, "Subcutaneous Tissue Responses in Rats to Injection of Fine Particles of Synthetic Hydroxyapatite Ceramic", *Biomedical Research*, Vol. 9, No. 2, pp. 95–111 (1988), discloses that subcutaneous injections of fine particles of hydroxyapatite ranging in diameter from about 0.65 to a few microns and scattered in the tissue were phagocytized by macrophages in extremely early stages. In contrast, larger particles measuring several microns in diameter were not phagocytized, but were surrounded by numerous macrophages and multinucleated giant cells. It was also observed that the small tissue responses to hydroxyapatite particles were essentially a non-specific foreign body reaction without any cell or tissue damage.

R. A. Appell, "The Artificial Urinary Sphincter and Periurethral Injections", *Obstetrics and Gynecology Report*. Vol. 2, No. 3, pp. 334–342, (1990), is a survey article disclosing various means of treating urethral sphincteric incompetence, including the use of injectables such as polytetrafluoroethylene micropolymer particles of about 4 to 100 microns in size in irregular shapes,. with glycerin and polysorbate. Another periurethral injectable means consists of highly purified bovine dermal collagen that is crosslinked with glutaraldehyde and dispersed in phosphate-buffered physiologic saline.

Politano et al., "Periurethral Teflon Injection for Urinary Incontinence", *The Journal of Urology*, Vol. 111, pp.

180–183 (1974), discloses the use of polytetrafluoroethylene paste injected into the urethra and the periurethral tissues to add bulk to these tissues to restore urinary control in both female and male patients having urinary incontinence.

Malizia et al, "Migration and Granulomatous Reaction After Periurethral Injection of Polytef (Teflon)", *Journal of the American Medical Association*, Vol. 251, No. 24, pp. 3277–3281, June 22–29 (1984), discloses that although patients with urinary incontinence have been treated successfully by periurethral injection of polytetrafluoroethylene paste, a study in continent animals demonstrates migration of the polytetrafluoroethylene particles from the inspection site.

Claes et al, "Pulmonary Migration Following Periurethral Polytetrafluoroethylene Injection for Urinary Incontinence", *The Journal of Urology*, Vol. 142, pp. 821–2, (September 1989), confirms the finding of Malizia in reporting a case of clinically significant migration of polytetrafluoroethylene paste particles to the lungs after periurethral injection.

Ersek et al, "Bioplastique: A New Textured Copolymer Microparticle Promises Permanence in Soft-Tissue Augmentation", *Plastic and Reconstructive Surgery*, Vol. 87, No. 4, pp. 693–702, (April 1991), discloses the use of a biphasic copolymer made of fully polymerized and vulcanized methylmethylpolysiloxane mixed with a plasdone hydrogel, and used in reconstructing cleft lips, depressed scars of chicken pox and indentations resulting from liposuction, glabella frown wrinkles and soft tissue augmentation of thin lips. The biphasic copolymer particles were found to neither migrate nor become absorbed by the body were textured and had particle sizes varying from 100 to 600 microns.

Lemperle et al. "PMMA Microspheres for Intradermal Implantiation: Part I. Animal Research", *Annals of Plastic Surgery*, Vol. 26, No. 1, pp. 57–63, (1991), discloses the use of polymethylmethacrylate microspheres having particle sizes of 10 to 63 microns in diameter used for correction of small deficiencies within the dermal corium to treat wrinkles and acne scars.

Kresa et al, "Hydron Gel Implants in Vocal Cords", *Otolaryngology Head and Neck Suraery*, Vol. 98. No. 3, pp. 242–245, (March 1988), discloses a method for treating vocal cord adjustment where there is insufficient closure of the glottis which comprises introducing a shaped implant of a hydrophilic gel that has been previously dried to a glassy, hard state, into the vocal cord.

Hirano et al, "Transcutaneous Intrafold Injection for Unilateral Vocal Cord Paralysis: Functional Results", *Ann. Otol. Rhinol. Laryngol.*, Vol. 99, pp. 598–604 (1990), discloses the technique of transcutaneous intrafold silicone injection in treating glottic incompetence caused by unilateral vocal fold paralysis. The silicone injection is given under a local anesthetic with the patient in a supine position, wherein the needle is inserted through the cricothyroid space.

Hill et al, "Autologous Fat Injection for Vocal Cord Medialization in the Canine Larynx", *Laryngoscope*, Vol. 101, pp. 344–348 (April 1991), discloses the use of autologous fat as an alternative to Teflon® collagen as the implantable material in vocal cord medialization, with a view to its use as an alternative to non-autologous injectable material in vocal cord augmentation.

Mikaelian et al, "Lipoinjection for Unilateral Vocal Cord Paralysis", *Laryngoscope*, Vol. 101, pp. 4654–68 (May 1991), discloses that the commonly used procedure of injecting Teflon® paste to improve the caliber of voice in unilateral vocal cord paralysis has a number of drawbacks, including respiratory obstruction from overinjected Teflon® and unsatisfactory voice quality. In this procedure, lipoinjection of fat commonly obtained from the abdominal wall appears to impart a soft bulkiness to the injected cord while allowing it to retain its vibratory qualities. The injected fat is an autologous material which can be retrieved if excessively overinjected.

Strasnick et al, "Transcutaneous Teflon® Injection for Unilateral Vocal Cord Paralysis: An Update", *Laryngoscope*, Vol. 101, pp. 785–787 (July 1991), discloses the procedure of Teflon® injection to restore glottic competence in cases of paralytic dysphonia.

SUMMARY OF THE INVENTION

In accordance with the present invention, there is provided a permanent, biocompatible material for soft tissue augmentation, and methods for its use. The biocompatible material comprises a matrix of smooth, rounded, substantially spherical, finely divided particles of a biocompatible ceramic material, close to or in contact with each other, which provide a scaffold or lattice for autogenous, three dimensional, randomly oriented, non-scar soft tissue growth at the augmentation site. The augmentation material can be homogeneously suspended, for example, in a biocompatible, resorbable lubricious gel carrier comprising, e.g., a polysaccharide. This serves to improve the delivery of the augmentation material by injection to the tissue site where augmentation is desired. The augmentation material is especially suitable for urethral sphincter augmentation, for treatment of incontinence, for filling soft tissue voids, for creating soft tissue blebs, for the treatment of unilateral vocal cord paralysis, and for mammary implants. It can be injected intradermally or subcutaneously or can be implanted.

DESCRIPTION OF THE DRAWINGS

In the accompanying drawings.

DESCRIPTION OF THE PREFERRED EMBODIMENTS

In instances of urinary incontinence, such as stress incontinence in women, or after a prostatectomy in men, it is necessary to compress the urethra to assist the sphincter muscle in closing to avoid leakage of urine from the bladder.

The soft tissue augmentation material of the present invention comprises an injection system which can be used to add bulk and localize compression to the sphincter muscle/urethra, thereby reducing the lumen size through one or more injections of the augmentation material and thus substantially reduce or eliminate urinary stress incontinence due to incompetent sphincters in females and males.

The augmentation material can also be used in filling and smoothing out soft tissue defects such as pock marks or scars. Further use for the augmentation material can be for intracordal injections of the laryngeal voice generator by changing the shape of this soft tissue mass. The procedure involves delivering the augmentation material to the site of treatment, preferably by injection.

The augmentation material can also be used for mammary implants, and can be encased in a suitable shell made of a polymeric material such as polyurethanes, ethylene-propylene diene monomers, ethylene-propylene rubbers, polyolefins, and silicone elastomers. It can also be used without a shell since the augmentation material does not migrate and remains in a particular area or bolus.

Figure 1:
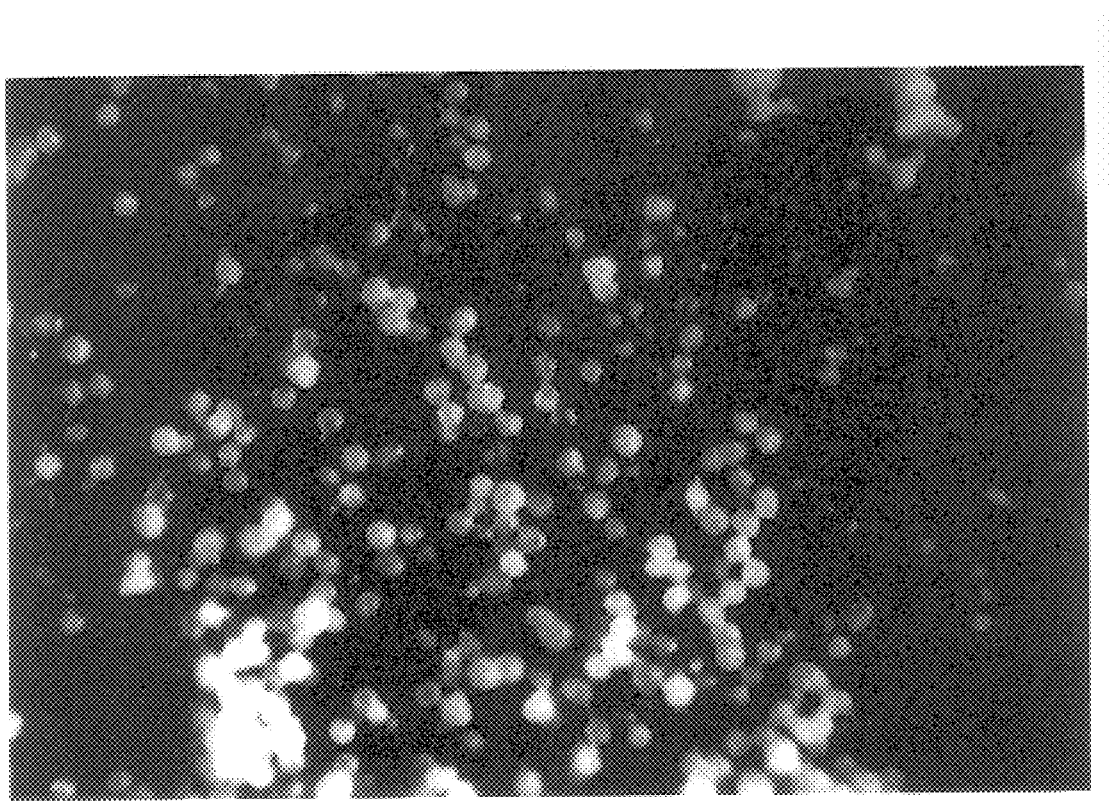
FIG. 1 is a photomicrograph of smooth, round calcium hydroxyapatite particles at 40× magnification.

The inventive augmentation material comprises smooth rounded, substantially spherical, particles of a ceramic material. The term "substantially spherical" refers to the fact that while some of the present particles may be spheres, most of the particles of the present invention are sphere-like in their shape, i.e., they are spheroidal. FIG. 1 is illustrative of these spheroidal or substantially spherical characteristics. The terms "rounded" or "smooth, rounded" as used herein refers to the fact even though the present particles are not perfect spheres, they do not have any sharp or angular edges. The particles must be sufficiently large so as to avoid phagocytosis, as is further discussed below. As an upper limit the particles can be any size suitable for the desired soft tissue augmentation. However, it is understood that for introduction by injection the upper limit on particle size will be dictated by the particular injection equipment employed. That is, the particles must be sufficiently small so as to avoid aggregation and clogging of the syringe when being injected. A typical range for injection is from about 35 to 150 microns, preferably in a narrow particle size range extending not more than about 35 microns, and more preferably extending not more than about 10 to 30 microns, and most preferably having substantially equivalent particle sizes. For example, the ceramic material can have a uniform particle size distribution of about 35 to 65 microns, or 75 to 100 microns or 100 to 125 microns. These are meant to be exemplary and not limiting. Other narrow particle size ranges within the overall size range of 35 to 150 microns can also be used. In discussing these ranges, it should be understood that as a practical matter, a small amount of particles outside the desired range may be present in a sample of the present augmentation material. However, most of the particles in any given sample should be within the desired range. Preferably, 90% of the particles are within the desired range and most preferably 95–99% are within the range.

The finely divided ceramic augmentation material is substantially non-resorbable so that repetitious corrections are not necessary. By "substantially non-resorbable" is meant that although some dissolution of the augmentation material may take place over time, it is sufficiently slow so as to allow for replacement with growing tissue cells. There is no antigenic response because there are no amino acids as in collagen and fibrinogen. The ceramic material is highly biocompatible and can be injected through an 18 gauge or smaller opening syringe.

The preferred ceramic material is calcium hydroxyapatite, also known as basic calcium orthophosphate, or calcium hydroxylapatite, and is the natural mineral phase of teeth and bones. As an implant material, granular calcium hydroxyapatite, which is a sintered polycrystalline composite of calcium phosphate, has proven to be highly compatible in tissue.

One method for preparing dense, rounded or substantially spherical ceramic particles such as calcium hydroxyapatite is by spray drying a slurry of about 20 to 40 weight % submicron particle size calcium hydroxyapatite. This material is commercially available or can be prepared by means known in the art such as by low temperature crystallization methods, hydrothermal crystallization methods, solid-solid reaction and the like. The slurry can also include processing additives such as wetting agents and binders, on the order of about 1 to 5 weight %. Suitable wetting agents include polysorbate, sodium oxalate, ammonium polyelectrolyte. Suitable binders include polyvinyl alcohol, dextrin or carbowax.

The slurry is spray dried by pumping it through a nozzle to form globules that are forced through a column of heated air to remove the moisture. The agglomerated particles dry in substantially spherical shape and are collected at one end of the heated column.

The substantially spherical particles are then sintered in a crucible at temperatures of about 1050 to 1200° C. for at least one hour. To minimize further agglomeration, a presintering operation at about 800 to 1000° C. for about one hour can be employed.

After the presintering operation, the globular particles can be agitated or rolled to prevent the individual particles from sticking or clumping together. A rotary calcining furnace can be used for this purpose. This type of furnace rotates so that the agglomerated particles roll over one another during the sintering process thereby minimizing the clumping together of the particles. A commercial source of such spray dried particles is CeraMed Corp., Lakewood, Colo.

An alternative method for forming dense, spherical particles is by rotary agglomeration, wherein the fine, submicron ceramic particles, such as calcium hydroxyapatite, are placed on a large diameter rotating bowl that is at least about 3 feet in diameter.

The bowl is rotated on its axis at an angle of approximately thirty degrees, with its speed and angle of rotation adjusted so that the submicron particles roll across the face of the bowl. A fine spray of binder solution, such as those described above, is then sprayed on the particles at a rate which just wets the particles. The rolling action across the face of the bowl and the addition of the binder solution causes the particles to form small rolling agglomerates that grow in size as the operation continues. The operation is comparable to forming a large ball of snow by rolling a small snowball down a hill. The operating conditions, such as the size of bowl, speed of rotation, angle of rotation and amount of spray used which define the size and density of the agglomerates formed, are well known to those skilled in the art. The agglomerated spherical particles can then be sintered in a manner similar to the spray dried agglomerates.

The resulting sintered spherical particles can then be separated and classified by size by means of well known sieving operations through specifically sized mesh screens. The particle size distribution and density can also be evaluated to ensure suitability for a particular application. A commercial source of such rotary agglomerated particles is CAM Implants, Leiden, The Netherlands.

Further surface refining or smoothing can be accomplished by a milling operation, such as ball milling. Extra mini-grinding media can be used, but to minimize contamination, the spherical particles can be milled on themselves. This can be done in a standard jar mill or an inclined rotation mill by adding sufficient amounts of purified water to the particles to ensure that the particles roll evenly over each other. This can be done for long periods such as several days to make the surface smooth on the round agglomerates. If the starting agglomerates are not round, they can be made smooth but not round by rolling. Irregularly shaped agglomerates, although having a smooth surface, can jam, obstruct or significantly increase the injection force on a syringe needle when injected into tissue.

The agglomerated spherical particles can also be washed free of small particles by using an inclined rotation mill. This can be done by placing the agglomerates in the mill with purified water and rolled for a sufficient time, such as one hour. The supernate is then poured off and more purified water is added. The process is repeated until the supernate is relatively clear after a rotating cycle, and usually takes about three or four operations.

The methods described above are suitable for any ceramic materials which may be employed.

A smooth surface on the individual round, spherical particles is important to reduce and minimize surface porosity. Surface smoothness can be improved by finishing operations known in the art, such as surface milling and the like. It is preferred that such smoothing operations be capable of minimizing surface irregularities on the individual particles so that the surface appears similar to that of a smooth round bead when viewed under a microscope at 40x magnification. This is apparent from FIG. 1, which is a photomicrograph of calcium hydroxyapatite particles having a particle size distribution of 38 to 63 microns. The smooth, round substantially spherical and non-porous surface is readily evident.

The ceramic particles are preferably smooth, hard, rounded particles, having a density on the order of about 75 to 100%, and preferably about 95 to 100% of the theoretical density of desired ceramic material, e.g., calcium hydroxyapatite. The finishing operations can also minimize the surface porosity of the calcium hydroxyapatite particles to less than about 30%, and preferably less than about 10%. This is preferred, because by minimizing surface porosity, particles with smooth surfaces can be obtained, thereby eliminating jagged, irregular surfaces and maximizing the ability of the smooth, round particles to flow easily in contact with each other.

Although this invention is described in terms of calcium hydroxyapatite, other suitable materials useful herein include, but are not limited to, calcium phosphate-based materials, alumina-based materials and the like. Examples include, but are not limited to, tetracalcium phosphate, calcium pyrophosphate, tricalcium phosphate, octacalcium phosphate, calcium fluoroapatite, calcium carbonate apatite, and combinations thereof. Other equivalent calcium based compositions can also be used such as calcium carbonate, and the like.

As noted, the individual ceramic particles used in the present invention have a generally smooth, round, preferably spherical shape, in contrast to particles with more textured porous surfaces or openings, and having jagged, irregular shapes or shapes with straight edges. The smooth round shape enables the ceramic particles to be more easily extruded and to flow with reduced friction from a syringe into the tissue site where soft tissue augmentation is desired. Once at the tissue site, the ceramic particles provide a matrix or scaffolding for autogenous tissue growth.

As mentioned above, particle sizes in the range of about 35 to 150 microns are optimal to minimize the possibility of particle migration by phagocytosis and to facilitate injectability. Phagocytosis occurs where smaller particles on the order of 15 microns or less become engulfed by the cells and removed by the lymphatic system from the site where the augmentation material has been introduced into the tissues, generally by injection.

At the lower end, particles greater than 15 microns and typically 35 microns or above are too large to be phagocytosized, and can be easily separated by known sizing techniques. Thus, it is relatively simple to produce the narrow or equivalent particle size ranges that are most desirable for use in this invention.

It is also desirable to use a narrow or equivalent particle size range of ceramic particles due to the fact that a distribution of such smooth, round, substantially spherical particles reduces friction, and facilitates the ease of injecting the particles by needle from a syringe into the skin tissue at the desired augmentation site. This is in contrast to the use of the more porous, textured, irregularly shaped particles which tend to increase the frictional forces, and are much more difficult to deliver by injection.

As discussed above, the particle size distribution, or range of particle sizes of the ceramic material within the overall range of 35 to 150 microns is preferably minimized to a more narrow or equivalent particle size range. This maximizes the intraparticle void volume, or interstitial volume, into which autogenous tissue growth, stimulated by the presence of the augmentation material, can occur. A greater interstitial volume exists between particles that are equivalent in size, compared with particles having a variable size distribution. In the context of this invention, the interstitial volume is the void space existing between particles of the augmentation material that are close to or in contact with each other.

For example, in crystalline lattice structures such as face centered cubic, body centered cubic and simple cubic, the percentage of interstitial void space, known as the atomic packing factor is 26%, 33%, and 48%, respectively. This is independent of the diameter of the atom or in this case, the particle. Since the ceramic particles never pack as tightly as the atoms in a crystalline lattice structure, the void volume would be even greater, thereby maximizing the growth of autogenous tissue.

To extend the analogy of the crystalline structure a step further, the interstitial opening defines the maximum size that a particle can fit into a normally occurring void space in the structure. The largest interstitial space is about 0.4 times the size of the mean ceramic particle in the particle size distribution.

Thus, if the particle size distribution is about 35 to 65 microns, the mean particle size would be 50 microns. The largest interstitial space would be 50x0.4=20 microns. Since no 20 micron size particles exist in the distribution, packing would be minimized. Similarly, with a particle size distribution of 75 to 125 microns, the mean particle size is 100 microns, and the largest interstitial space would be 100x0.4=40 microns. Since no 40 micron particles exist in the distribution, packing would also be minimized. Therefore, if the ceramic particles are restricted to a narrow particle size range or equivalent size distribution, there will be a maximizing of the void volume into which the autogenous tissue can grow.

Other suitable particle size distribution ranges include 35 to 40 microns, 62 to 74 microns and 125 to 149 microns, however, any other correspondingly narrow ranges can also be used.

In contrast, where there is a wide particle size distribution, there is a greater tendency for the particles to become densely packed since the smaller particles tend to group or migrate into the spaces between the larger particles. This results in less interstitial space available between the particles for the autogenous tissue such as fibroblasts and chondroblasts to infiltrate and grow.

The tissue growth where the augmentation material has a wide particle size distribution is denser and harder, because of the packing effect which occurs between the large and small particles. In contrast, the use of particles equivalent in size, or having a narrow particle size range of uniformly distributed particles increases the intraparticle void volume. This enables a maximum amount of autogenous or three dimensional randomly oriented non-scar soft tissue ingrowth to infiltrate the space or interstices between the particles. The more interstitial space that is available makes it more likely that the subsequent autogenous tissue growth stimulated by the presence of the augmentation material into the matrix or scaffolding provided by the augmentation material will closely resemble the original tissue in the immediate vicinity or locus of augmentation.

The process of soft tissue augmentation can occur by injecting or implanting the biocompatible augmentation material comprising the desired particle sizes of the desired ceramic material into the tissue at the desired augmentation site to form a bleb or blister. The subsequent autogenous tissue growth into the matrix provided by the augmentation material will most closely resemble the surrounding tissue in texture and properties. This is in contrast to that which occurs using known state-of-the-art procedures, where foreign body response is known to occur, typically with Teflon® augmentation where granulomas have been known to form.

Foreign body response is the body reaction to a foreign material. A typical foreign body tissue response is the appearance of polymorphonuclear leukocytes near the material followed by macrophages. If the material is nonbioreactive, such as silicone, only a thin collagenous encapsulation tissue forms. If the material is an irritant, inflammation will occur and this will ultimately result in granulation tissue formation. In the case of ceramic materials such as calcium hydroxyapatite, there is excellent biocompatibility resulting in tissue cell growth directly on the surface of the particles with a minimum of, or substantially no encapsulation.

Autogenous tissue is defined herein as any tissue at a specific defined location in the body, whose growth is stimulated by the presence of the matrix of the biocompatible augmentation material at the site where soft tissue augmentation is desired. Such autogenous tissue from augmentation in the area of the urethral sphincter would resemble existing tissue in the urethral sphincter. Autogenous tissue from augmentation in the larynx would resemble existing tissue in the glottis where the vocal apparatus of the larynx is located. Autogenous tissue from breast augmentation would resemble existing tissue in the mammaries, and so on. Autogenous tissue in the case of intradermal injections would resemble the dermis. In a similar manner, the augmentation material, by providing a three dimensional lattice can be used in surgical incisions or trauma to avoid linear, layered contractile scar formation.

As discussed above, the calcium hydroxyapatite particles used as the augmentation material are biocompatible and substantially non-resorbable. Thus, the soft tissue augmentation procedure is permanent. Moreover, the use of calcium hydroxyapatite does not require the strict rigorous precautions that are necessary when using other augmentation materials such as collagen which need refrigeration for storage, shipping and antigenicity testing.

The rounded, spherical smooth calcium hydroxyapatite particles enhance the biocompatibility to the autogenous tissue response into the particle matrix and substantially eliminates the potential for calcification. Jagged or irregular particles can irritate tissue and can cause calcification. In addition, surface porosity on the order of about 30 volume % or greater can also cause calcification because of the relative stability of the pores in the particles. Smooth, round, substantially non-porous particles maintain movement in the tissue. Thus, the autogenous tissue grown in the particle matrix where movement is maintained, does not calcify. In contrast, the porous sections of the individual particles are stationary relative to the particle, thus tissue infiltration into the pores is not subject to movement and calcification can occur.

The particulate ceramic material can be suspended in a biocompatible, resorbable lubricant, such as a cellulose polysaccharide gel to improve the delivery of the augmentation material by injection to the tissue site where augmentation is desired. Preferably, the gel comprises water, glycerin and sodium carboxymethylcellulose. The gel enables the ceramic particles to remain in suspension without settling for an indefinite period of time until used, more specifically, at least about 6 months. Other suitable lubricant compositions known in the art can also be employed.

In general, the ratio of water to glycerin in the gel can vary from about 10 to 100:90 to 0, preferably about 20 to 90:80 to 10, and most preferably about 25 to 75:75 to 25, respectively.

The viscosity of the gel can vary from about 20,000 to 200,000 centipoise, preferably about 40,000 to 100,000 centipoise as measured with a Brookfield Viscometer with RU#7 spindle at 16 revolutions per minute (rpm). It has been found that with gel viscositiesbelow about 20,000 centipoise the particles do not remain in suspension, and with gel viscosities above about 200,000 centipoise, the gel becomes too viscous for convenient mixing.

The sodium carboxymethycellulose included in the gel has a high viscosity rating. More specifically, the sodium carboxymethylcellulose preferably has a viscosity of about 1000 to 2800 centipoise in a 1% aqueous solution and can vary from about 0.25 to 5 weight %, preferably 1.25 to 3.25% of the combined water and glycerin in the gel.

Other polysaccharides can also be included such as cellulose, agar methylcellulose, hydroxypropyl methylcellulose, ethylcellulose, microcrystalline cellulose, oxidized cellulose, and other equivalent materials. Unexpectedly, formulating the augmentation particles of the present invention, particularly the calcium hydroxyapatite with sodium carboxymethylcellulose, provides a change in the surface morphology of the particles which is believed to enhance the physical and biocompatible properties of the material.

The gel is prepared by mixing the gel components at ambient conditions until all components are in solution. It is preferable to combine the glycerin and NaCMC components together first until a thoroughly mixed solution is obtained. The glycerin/NaCMC solution is then mixed together with the water until all components are in solution to form the gel. After the gel components have been thoroughly mixed, the gel is allowed to set for minimum of 4 hours, after which viscosity readings are taken to ensure that the gel has the desired viscosity.

While any lubricant can be employed, it has been found that certain materials, e.g., polysorbate surfactants, pectin, chondroitin sulfate and gelatin, are not able to suspend the ceramic particles for an indefinite amount of time and allow further processing or be as easy to inject in the same manner as the sodium carboxymethylcellulose. Thus, the sodium caarboxymethylcellulose materials is preferred.

The polysaccharide gel is biocompatible and able to maintain the particles of ceramic material in what amounts to a substantially permanent state of suspension so that the ceramic particulate/gel composition comprising the augmentation material does not require mixing before use. As already noted, the lubricious nature of the polysaccharide gel reduces the frictional forces generated by transferring the augmentation material from a syringe by injection into the tissue site.

In addition, the polysaccharides do not generate an antigenic response as do products containing amino acids. The polysaccharide gel is readily sterilizable and stable at ambient conditions and does not need refrigeration for storage and shipment, in contrast to systems used with collagen containing materials.

Sterilization is ordinarily accomplished by autoclaving at temperatures on the order of about 115° C. to 130° C., preferably about 120° C. to 125° C. for about 30 minutes to 1 hour. Gamma radiation is unsuitable for sterilization since it tends to destroy the gel. It has also been found that sterilization generally results in reduction of its viscosity. However, this does not adversely affect the suspension and therefore the extrusion force of the augmentation material through a syringe, nor does it affect the ability of the gel to hold the calcium hydroxyapatite particles in suspension, as long as the prescribed viscosity ranges for the gel are maintained.

After injection of the augmentation material into the tissue, the polysaccharide gel is harmlessly resorbed by the tissue, leaving the non-resorbable calcium hydroxyapatite matrix in place in the particular area or bolus, where it has been found to remain without migrating to other areas of the body. It generally takes an average of about 2 weeks for the polysaccharide to completely resorb.

Figure 2:
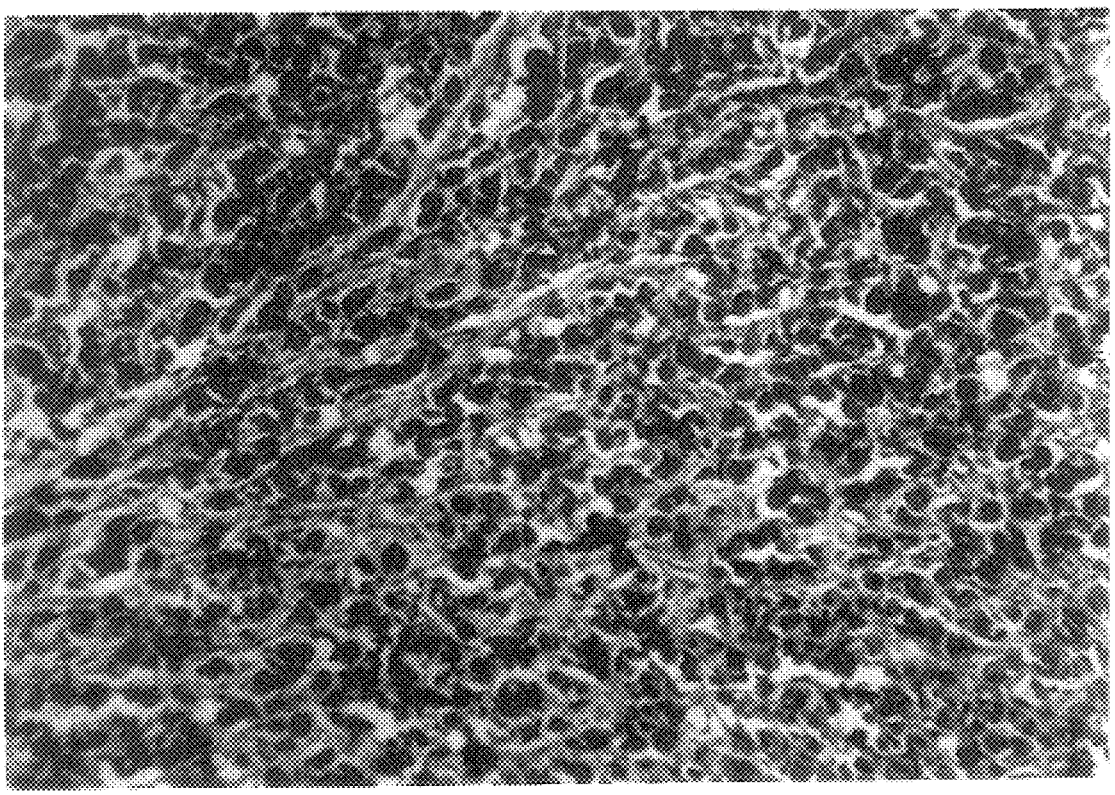
FIG. 2 is a photomicrograph of a histological section of rabbit tissue at 50× magnification showing fibroblastic infiltration.

FIG. 2 shows a histological section of rabbit tissue at 50× magnification which has been infiltrated with autogenous three dimensional, randomly oriented, non-scarring soft muscle tissue as a result of an injection of calcium hydroxyapatite particles having a uniform particle size distribution of 38 to 63 microns. The photomicrograph shows growth after 12 weeks. The histological section also demonstrates the biocompatibility of the calcium hydroxyapatite as the cells grow on the surface of the particles with minimal or substantially no foreign body response.

It has been found that the amount of calcium hydroxyapatite particles in the augmentation material can vary from about 15% to 50% by volume, and preferably about 25% to 47.5% and most preferably about 35% to 45% by volume of the total augmentation material, comprising the gel and the ceramic particles.

Preparations having above 50 volume % ceramic particles become viscous and care should be taken as to the selection of injection apparatus. As a lower limit the augmentation material of this invention should obviously contain a sufficient volume of ceramic particles to provide an effective base for tissue autogenous tissue growth. For most applications this is at least 15 volume %. By maintaining a volume % of about 35 to 45%, a correction factor of about 1:1 can be achieved, that is, the volume of autogenous tissue growth is roughly equivalent to the volume of particles introduced and shrinkage or expansion at the site of the soft tissue augmentation does not generally occur.

Also, within these parameters, the augmentation material can easily be injected through an 18 gauge or smaller syringe intradermally or subcutaneously. Because of the reduced frictional forces necessary to deliver the biocompatible augmentation material by injection to the desired tissue site, the size of the syringe used to transfer or inject the biocompatible augmentation material can be significantly reduced. This substantially eliminates the possibility of creating a needle trail through which leakage of the augmentation material from the injection site can occur after withdrawing the injection needle. Thus, the syringes used to inject the augmentation material can have reduced openings of less than 1,000 microns in diamter to a minimum of about 178 microns or less.

For example, an 18 gauge syringe having a diameter of about 838 microns, or a 20 gauge syringe having a diameter of about 584 microns, or a 22 gauge syringe having a diameter of about 406 microns, and even a 28 gauge syringe having a diameter of about 178 microns can be used, depending on the tissue site where augmentation is needed.

The lubricious suspension of augmentation material is prepared by simply mixing the desired amount of ceramic particles with the lubricious gel until a uniform, homogeneous suspension is reached. The consistency of the ceramic particles suspended in the lubricious gel is comparable to strawberry preserves, wherein the seeds and other solid parts of the strawberry, for all practical purposes, are comparable to the ceramic particles and remain substantially permanently suspended in the jelly preserve matrix.

The suspension of ceramic material in the lubricious gel is so stable, that centrifugation at forces on the order of 500 g's, that is, 500 times the force of gravity generally do not affect the stability of the suspension or cause it to settle out. The tendency, if any, for particles to settle out over a period of time would appear more likely to occur with the larger particle sizes on the order of 125 microns or larger. Thus, remixing the augmentation material at the time of injection or implantation is ordinarily not necessary. In addition, the polysaccharide gel lubricates the suspended ceramic particles so that the injection force on the syringe can be minimized when injecting the augmentation material.

The following examples show specific embodiments of the invention. All parts and percentages are by weight unless otherwise noted.

EXAMPLE 1

Preparation of the Gel

A mixture of 25% glycerin, 75% water, and 2.25% NaCMC (based on the combined weight of the water and glycerin) is prepared in the following manner:

87.90 g of glycerin and 7.91 g of NaCMC are combined in a vessel large enough to mix total mass. The mixture is then slowly added to 263.71 g of agitating water in a container large enough for batch size and allowed to mix, utilizing an electric mixer, for 30 minutes at a medium speed. The gel is allowed to set for a minimum of four hours.

EXAMPLE 2

Preparation of the Augmentation Composition

Aqueous glycerin/NaCMC gel (38.52 g, prepared in Example 1) are placed in a mixing container large enough for batch size, Smooth, rounded substantially spherical CaHA particles (74.86 g) having a uniform particle size of 37 to 63 microns are thoroughly blended, utilizing an electric mixer, for five minutes at a low speed until all the particles are homogeneously distributed in a uniform suspension in the gel.

EXAMPLE 3

In most instances it takes relatively little force to inject or extrude the augmentation composition, comprising the polysaccharide gel/particulate calcium hydroxyapatite suspension, into the air since there is relatively little resistance. However, greater forces were necessary to inject the augmentation composition into tissue, and this force is significantly influenced by the shape of the particulate material. This was exemplified by preparing sterilized suspensions of polysaccharide gel made of 75% water, 25% glycerin, and 2.25% sodium carboxymethylcellulose (based on the combined weight of the water and glycerin) with various volume percents of calcium hydroxyapatite particles having different shapes, following the procedure of Example 2. The thus prepared suspensions were placed in standard 3 cubic centimeter syringes. The force applied to the plunger to extrude the polysaccharide gel/particulate suspension at a rate of one inch per minute through an 18 gauge needle was then measured. The force was also measured with the needle inserted into turkey gizzard tissue as an analogy as it would be used clinically. The spray dried particles of calcium hydroxyapatite, regardless of their shape, had a smooth, uniform appearance under microscopic examination at 40× magnification. The particles were uniformly distributed within the range of particle sizes. The results are tabulated in Table 1, which follows:

TABLE 1

Calcium Hydroxyapatite Particles in the Gel

| Size, Microns | Particle Shape | Volume. % Solids | Force, lbs Air | Force, lbs Tissue |
| --- | --- | --- | --- | --- |
| 38 to 63 | Spherical/Smooth | 35 | 4.5 | 6.0 |
| 38 to 63 | Spherical/Smooth | 40 | 5.9 | 7.2 |
| 38 to 63 | Irregular | 40 | 8.0* | 9.6* |
| 74 to 100 | Irregular/Smooth | 37 | 5.5 | >30 |
| 74 to 100 | Irregular/Smooth | 41 | >30 | >30 |
| 74 to 100 | Spherical/Smooth | 42 | 4.8 | 5.5 |

*Average. Inconsistent results due to complete obstruction of needle that sporadically occurred during the tests., requiring replacement of needle.

This data correlated with animal experimentation where it was not possible to inject irregular particles into tissue even when the percent solids were reduced below 25 volume % or a 16 gauge needle was used.

EXAMPLE 4

Sterilized samples of polysaccharide gel/particulate calcium hydroxyapatite suspensions were prepared using a series of designated particle size ranges. The distribution of particles was uniform within each range of particle sizes. The particles were smooth, round calcium hydroxyapatite, and the gel had the same constituency as Example 1. The calcium hydroxyapatite particles occupied 36 volume % of the suspension. The extrusion force into the air for each suspension containing each designated range of particle sizes was measured using a standard 3 cubic centimeter syringe in the same manner as in Example 3. The results are tabulated in Table 2, which follows, and demonstrate that little. difference in the extrusion force occurs as the particle size increases, as long as the particle sizes are uniform and maintained in a narrow distribution range.

TABLE 2

| Size Distribution, microns | Extrusion Force, lbs |
| --- | --- |
| 40–60 | 2.3 |
| 62–74 | 2.0 |
| 40–74 | 2.6 |

TABLE 2-continued

| Size Distribution, microns | Extrusion Force, lbs |
| --- | --- |
| 82–100 | 2.3 |
| 100–125 | 2.2 |
| 125–149 | 2.4 |
| 100–149 | 2.4 |

EXAMPLE 5

Sodium carboxymethylcellulose, water and glycerin in various weight percents were formulated into four different gels following the procedure of Example 1, except for the use of different proportions. Each gel was then blended with about 40 volume % calcium hydroxyapatite particles having a distribution of 38 to 63 microns. The gel/particle blends were then placed in standard 3 cubic centimeter syringes fitted with 18 gauge, 20 gauge and 22 gauge needles. The extrusion force of the blend into the air was measured in the same manner as in Example 3. The results appear below in Table 3.

TABLE 3

| Weight % | | | Force, lbs | | |
| --- | --- | --- | --- | --- | --- |
| % NaCMC* | Glycerin | Water | 18 gauge | 20 gauge | 22 gauge |
| 1.0 | 60 | 40 | 3.6 | 6.4 | 7.7 |
| 1.5 | 50 | 50 | 4.0 | 5.8 | 8.2 |
| 2.0 | 30 | 70 | 4.1 | 6.3 | 7.7 |
| 2.0 | 40 | 60 | 4.8 | 7.0 | 9.2 |

*Sodium carboxymethylcellulose. Weight % of sodium carboxymethylcellulose based on total weight of glycerin and water.

What is claimed is:

1. A process for producing substantially smooth and substantially spherical, finely divided particles of a biocompatible ceramic material with minimized surface porosity, comprising the steps of:

agglomerating fine, submicron ceramic particles using a rotary technique; and sintering the agglomerated particles, the resulting biocompatible ceramic particles having a size of largest diameter for each particle in the range of about 15 to 150 microns and a density of about 75 to 100% of the theoretical density of the biocompatible ceramic material, wherein the rotary technique comprises the steps of:
placing a plurality of submicron ceramic particles in a rotating bowl;
rotating the bowl at a speed and angle such that the plurality of submicron ceramic particles roll across the face of the bowl; and
applying a fine spray of binder solution to the plurality of submicron ceramic particles during the rotation of the bowl, and wherein the sintering step comprises:
a presintering operation at about 800 to 1,000° C. for at least one hour; and
sintering the agglomerated particles at a temperature of about 1,050 to 1,200° C. for at least one hour.

2. The process of claim 1, further comprising the step of agitating the agglomerated particles after the presintering operation.

3. The process of claim 2, wherein the agglomerated particles are rolled to prevent individual particles from sticking or clumping together.

4. The process of claim 3, wherein the agglomerated particles are sintered in a rotary furnace whereby the agglomerated particles roll over one another during the sintering process thereby minimizing clumping together of the particles.

5. The process of claim 1, further comprising the steps of separating and classifying the sintered particles so that the biocompatible ceramic particles have a narrow, substantially equivalent particle size range.

6. The process of claim 5, wherein the step of separating and classifying the sintered particles comprises separating and classifying the sintered particles into a particle size range of largest diameter for each particle of about 35 to 65 microns, 35 to 40 microns, 62 to 74 microns or 125 to 149 microns.

7. The process of claim 1, further comprising the step of surface refining or smoothing the agglomerated particles.

8. The process of claim 7, wherein the step of surface refining or smoothing the agglomerated particles comprises milling the agglomerated material.

9. The process of claim 1, further comprising the step of washing the agglomerated particles to remove small particles.

10. The process of claim 9, wherein the washing comprises rolling the agglomerated particles in water in a rotation mill and removing supernatant containing the small particles.

11. The process of claim 1, wherein the bowl is rotated on its axis at an angle of approximately thirty degrees.

12. The process of claim 11, wherein the bowl is about three feet in diameter.

13. The process of claim 1, wherein the submicron ceramic particles comprise calcium hydroxyapatite particles.

14. The process of claim 1, wherein the binder solution includes at least one of polyvinyl alcohol, dextrin and carbowax.

* * * * *